(12) United States Patent
Meyerson et al.

(10) Patent No.: US 12,369,794 B2
(45) Date of Patent: Jul. 29, 2025

(54) MICROVASCULAR ASSESSMENT USING EYE IMAGING DEVICE

(71) Applicant: Welch Allyn, Inc., Skaneateles Falls, NY (US)

(72) Inventors: Craig M. Meyerson, Syracuse, NY (US); Stacey A. Fitzgibbons, Dewitt, NY (US); Allen R. Hart, Knoxville, TN (US); David L. Ribble, Indianapolis, IN (US); Heather Whitt, Kirkville, NY (US); Gene J. Wolfe, Pittsford, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 804 days.

(21) Appl. No.: 17/368,041

(22) Filed: Jul. 6, 2021

(65) Prior Publication Data
US 2022/0039653 A1 Feb. 10, 2022

Related U.S. Application Data

(60) Provisional application No. 63/063,593, filed on Aug. 10, 2020.

(51) Int. Cl.
*A61B 3/14* (2006.01)
*A61B 3/00* (2006.01)
(Continued)

(52) U.S. Cl.
CPC ............ *A61B 3/14* (2013.01); *A61B 3/0041* (2013.01); *A61B 3/0075* (2013.01); *G16H 40/67* (2018.01); *G16H 50/30* (2018.01)

(58) Field of Classification Search
CPC ... A61B 1/06; A61B 1/00147; A61B 1/00002; A61B 1/313; A61B 3/00; A61B 5/00;
(Continued)

(56) References Cited

U.S. PATENT DOCUMENTS

| 2002/0052551 A1 | 5/2002 | Sinclair et al. |
| 2008/0059234 A1 | 3/2008 | Hildebrand et al. |

(Continued)

FOREIGN PATENT DOCUMENTS

| CN | 108836259 A | 11/2018 |
| CN | 111345776 A | 6/2020 |

(Continued)

OTHER PUBLICATIONS

European Search Report, Application No. EP 21 19 0320 dated Dec. 9, 2021, 9 pages.

(Continued)

*Primary Examiner* — Brandi N Thomas
(74) *Attorney, Agent, or Firm* — Merchant & Gould P.C.

(57) ABSTRACT

A system for capturing one or more eye images includes an eye imaging device having a camera configured to capture the eye images. The system determines a workflow for capturing the eye images using the eye imaging device. The workflow is determined based on a risk score for a given patient. The system performs the workflow on the eye imaging device to capture the eye images, conducts a microvascular assessment based on the captured eye images, and adjusts the risk score based on the microvascular assessment.

19 Claims, 11 Drawing Sheets

(51) Int. Cl.
 *G16H 40/67* (2018.01)
 *G16H 50/30* (2018.01)

(58) Field of Classification Search
 CPC .... A61B 34/00; A61B 2576/00; G06V 10/00; G06F 9/00; G06F 8/00; G06F 3/00; G06F 7/00; G02B 5/00; G02B 3/00; G02B 7/00; G02B 21/00; G02B 23/00; G02B 25/00
 See application file for complete search history.

(56) References Cited

U.S. PATENT DOCUMENTS

| | | |
|---|---|---|
| 2011/0242306 A1 | 10/2011 | Bressler et al. |
| 2017/0100029 A1 | 4/2017 | Faber |
| 2017/0340483 A1 | 11/2017 | Rill et al. |
| 2018/0182476 A1* | 6/2018 | Babu ................... G06F 3/0482 |
| 2019/0357769 A1 | 11/2019 | Wang |
| 2020/0196861 A1 | 6/2020 | Hart et al. |
| 2020/0202529 A1* | 6/2020 | Hart ..................... A61B 3/0025 |
| 2020/0204710 A1 | 6/2020 | Myers et al. |
| 2020/0305783 A1 | 10/2020 | Baker et al. |
| 2020/0335190 A1 | 10/2020 | Chung et al. |
| 2021/0059597 A1 | 3/2021 | Chung et al. |

FOREIGN PATENT DOCUMENTS

| | | | |
|---|---|---|---|
| EP | 3378377 | * 9/2018 | ........... A61B 3/0025 |
| JP | 2019066846 A | 4/2019 | |

OTHER PUBLICATIONS

Chinese Office Action for Application No. 202110838747.4 mailed Jan. 23, 2025.

* cited by examiner

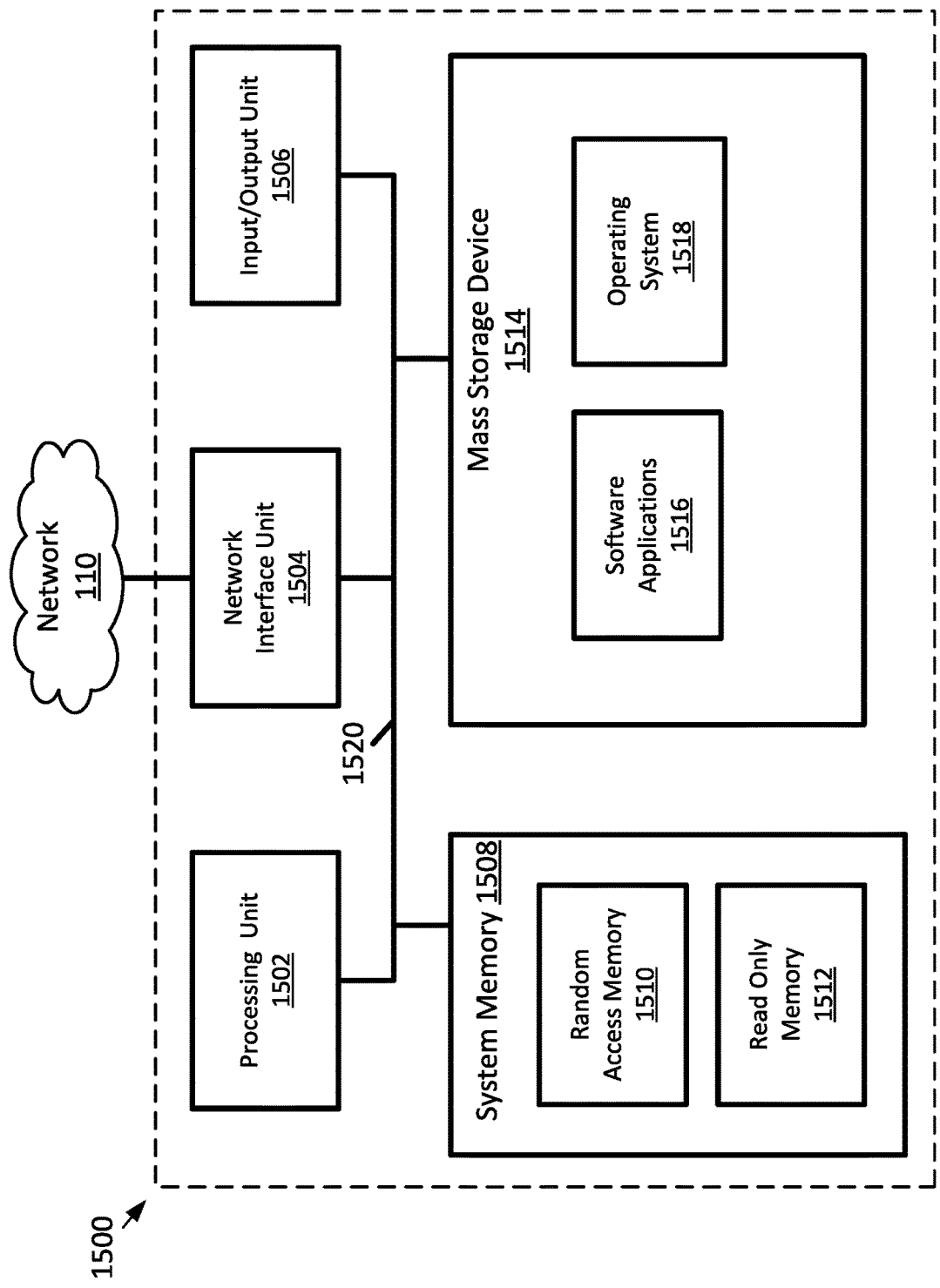

MICROVASCULAR ASSESSMENT USING EYE IMAGING DEVICE

BACKGROUND

It is often observed that certain patients diagnosed with a disease have mild symptoms at the onset of the disease, but then experience a rapid deterioration. For example, patients diagnosed with sepsis or coronavirus can have mild symptoms that later lead to acute respiratory distress, multiple-organ failure, septic shock, and blood clots.

In patients diagnosed with sepsis or coronavirus, endothelial cell malfunction may occur, causing microvascular problems and rapid deterioration of the patient's condition. Changes in the microvasculature may precede changes to macro vital signs such as heart rate, respiration rate, and blood pressure, and can be helpful to predict patient deterioration.

SUMMARY

The present disclosure generally relates to an eye imaging device and methods of using the device. In one possible configuration, the eye imaging device provides an enhanced risk score for patient deterioration, and patient access to the device is improved. Various aspects are described in this disclosure, which include, but are not limited to, the following aspects.

In one aspect, a system for capturing one or more eye images comprises: an eye imaging device having a camera configured to capture the eye images; and a computing device having at least one processor, and a memory storing instructions which, when executed by the at least one processor, cause the system to: determine a workflow for capturing the eye images using the eye imaging device, the workflow determined based on a risk score for a given patient; perform the workflow on the eye imaging device to capture the eye images; conduct a microvascular assessment based on the captured eye images; and adjust the risk score based on the microvascular assessment.

In another aspect, a method for capturing one or more eye images comprises: determining a workflow for capturing the one or more eye images using an eye imaging device, the workflow determined based on a risk score for a given patient; performing the workflow on the eye imaging device to capture the eye images; conducting a microvascular assessment based on the captured eye images; and adjusting the risk score based on the microvascular assessment.

In another aspect, a non-transitory computer readable storage media includes computer readable instructions which, when read and executed by a computing device, cause the computing device to: determine a workflow for capturing one or more eye images using an eye imaging device, the workflow determined based on a risk score for a given patient; perform the workflow on the eye imaging device to capture the one or more eye images; conduct a microvascular assessment based on the captured eye images; and adjust the risk score based on the microvascular assessment.

DESCRIPTION OF THE FIGURES

The following drawing figures, which form a part of this application, are illustrative of the described technology and are not meant to limit the scope of the disclosure in any manner.

FIG. 15 schematically illustrates an example of a computing device which can be used to implement aspects of the eye imaging device of FIG. 2.

DETAILED DESCRIPTION

Figure 1:
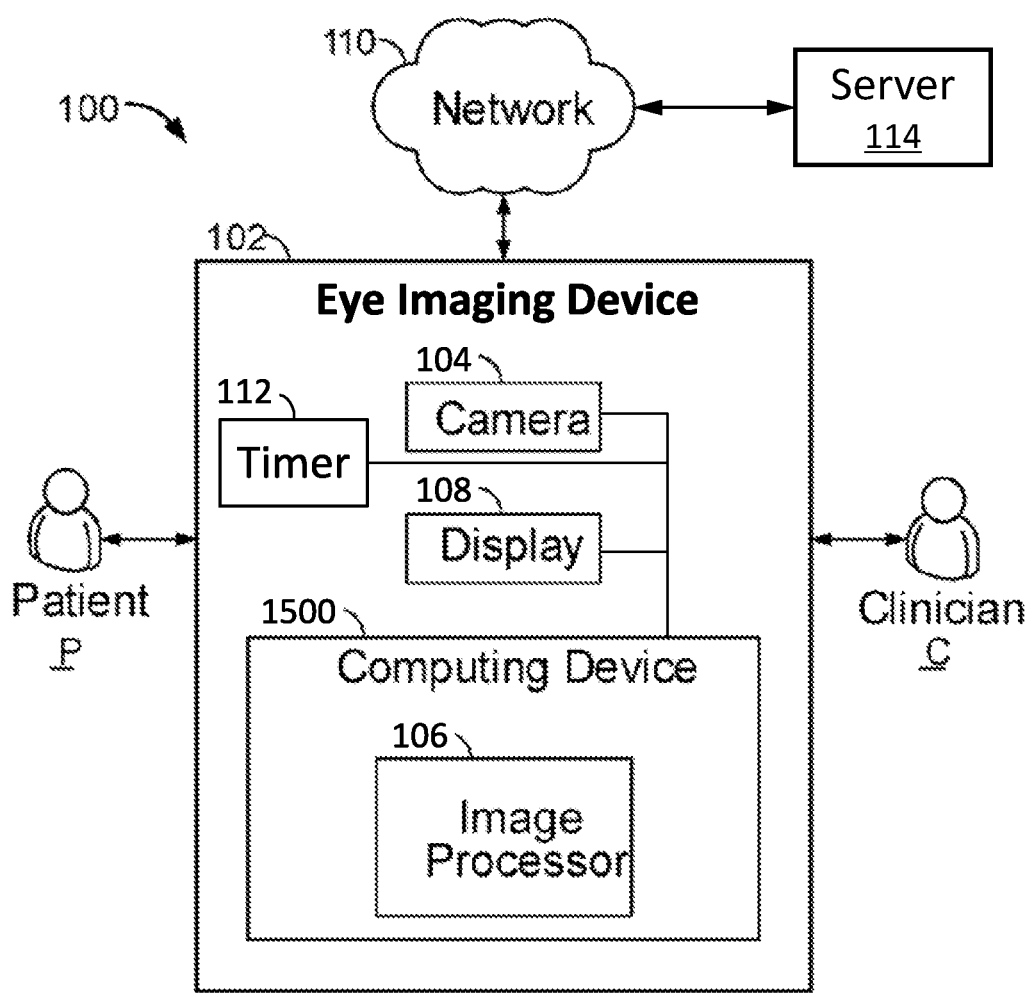
FIG. 1 schematically illustrates an example of a system for capturing fundus images.
Figure 2:
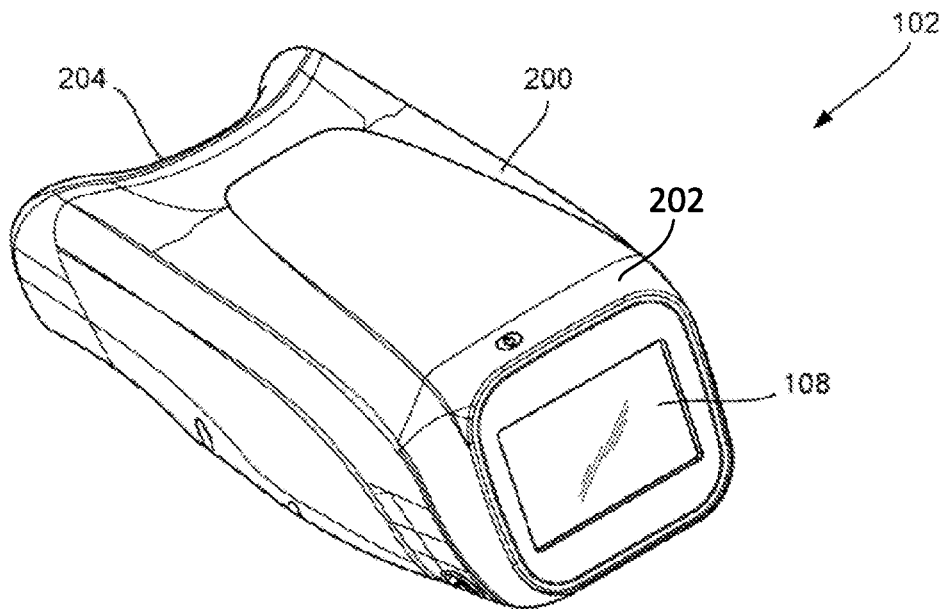
FIG. 2 is an isometric view of an example of an eye imaging device in FIG. 1

FIG. 1 schematically illustrates an example system 100 for capturing images of the eye including the fundus. Similar systems are described in U.S. patent application Ser. No. 16/443,234 filed on Jun. 17, 2019, U.S. patent application Ser. No. 16/229,939 filed on Dec. 21, 2018, and U.S. patent application Ser. No. 16/230,315 filed on Dec. 21, 2018, all of which are hereby incorporated by reference in their entireties.

In the example illustrated in FIG. 1, the system 100 includes a patient P, an eye imaging device 102, a computing device 1500 including an image processor 106, a camera 104 in communication with the computing device 1500, a display 108 in communication with the computing device 1500, a timer 112 in communication with the computing device 1500, and a network 110. An embodiment of the example eye imaging device 102 is shown and described in more detail below with reference to FIGS. 2-6.

In certain embodiments, a clinician C can use the display 108 of the eye imaging device 102 to capture and view one or more images of the patient P's eyes. Alternatively, the patient P can use the eye imaging device 102 him/herself such that assistance from the clinician C is not required to capture the one or more images of the patient P's eyes.

Accordingly, the eye imaging device 102 can be used by the clinician C or patient P to create a set of digital images of the patient P's eyes. In certain examples, the digital images of the patient P's eyes include images of the fundus.

As used herein, "fundus" refers to the eye fundus and includes the retina, optic nerve, macula, vitreous, choroid, and posterior pole.

The eye imaging device 102 can be used to capture one or more images of the patient P's eyes for screening for an eye disease such as diabetic retinopathy, monitoring progression of diseases that may affect the microvasculature such as sepsis or coronavirus, and determining a disease risk assessment that predicts a likelihood of patient deterioration from the disease.

One technique for fundus imaging requires mydriasis, or the dilation of the patient's pupil, which can be painful and/or inconvenient to the patient P. The eye imaging device 102 does not require a mydriatic drug to be administered to the patient P before imaging, although the device can image the fundus if a mydriatic drug has been administered.

The eye imaging device 102 includes a camera 104 in communication with the image processor 106. The camera 104 is a digital camera including a lens, an aperture, and a sensor array. The lens of the camera 104 can be a variable focus lens, such as a lens moved by a step motor, or a fluid lens, also known as a liquid lens. In certain embodiments, the camera 104 records images of the fundus one eye at a time. In other embodiments, the camera 104 records images of both eyes substantially simultaneously. In such embodiments, the eye imaging device 102 can include two separate cameras, one for each eye.

The image processor 106 is operatively coupled to the camera 104 and is configured to communicate with the display 108 and network 110. The image processor 106 regulates the operation of the camera 104 and display 108. An example computing device that includes a processing unit such as the image processor 106, is shown in more detail in FIG. 15.

The example eye imaging device 102 is connected to a network 110. The network 110 may include any type of wireless network, a wired network, or any communication network known in the art. For example, wireless connections can include cellular network connections and connections made using protocols such as 802.11a, b, and/or g. In other examples, a wireless connection can be accomplished directly between the eye imaging device 102 and an external display using one or more wired or wireless protocols, such as Bluetooth, Wi-Fi Direct, radio-frequency identification (RFID), or Zigbee. Other configurations are possible.

The timer 112 can be used to let the clinician C or the patient P know when an image or set of images should be taken by the eye imaging device 102. The use of the timer 112 will be described in more detail below with reference to the method 1400 of FIG. 14.

In certain embodiments, the image processor 106 processes the one or more images captured by the camera 104 to generate an output such as a disease risk assessment that predicts a likelihood of patient deterioration from a disease based on a microvascular assessment. Thereafter, the eye imaging device 102 can utilize the network 110 to transfer the output to a server 114 that is remotely located with respect to the Patient P and clinician C.

In alternative embodiments, the image processor 106 transfers the one or more captured images to the server 114 via the network 110, and the server 114 processes the one or more images captured by the camera 104 and generates the output. In further alternative embodiments, the processing of the one or more images captured by the camera 104 is shared between the image processor 106 of the eye imaging device 102 and the server 114 such that some processing of the one or more captured images is performed by the image processor 106, while further processing of the one or more captured images is performed by the server 114.

FIGS. 2-5 show an example of the eye imaging device 102 that includes a housing 200 that supports the components of the device. The housing 200 supports the display 108 at a first end 202 and is configured to engage one or both eyes of the patient P at an opposite end 204. As will be described herein, the eye imaging device 102 can be used to implement one or more of the described methods for imaging of the fundus.

Figure 3:
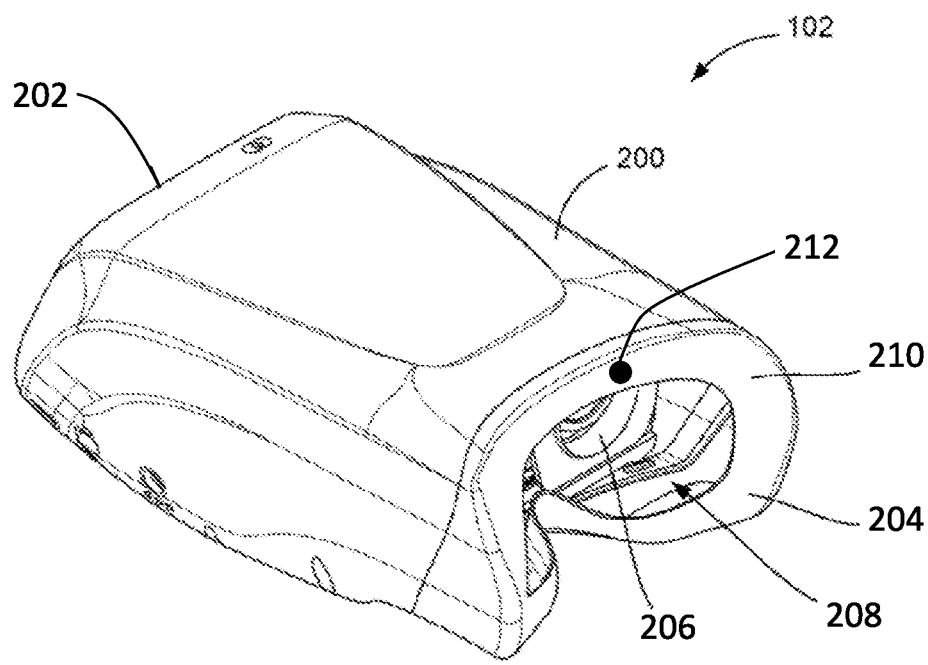
FIG. 3 is another isometric view of the eye imaging device of FIG. 2
Figure 5:
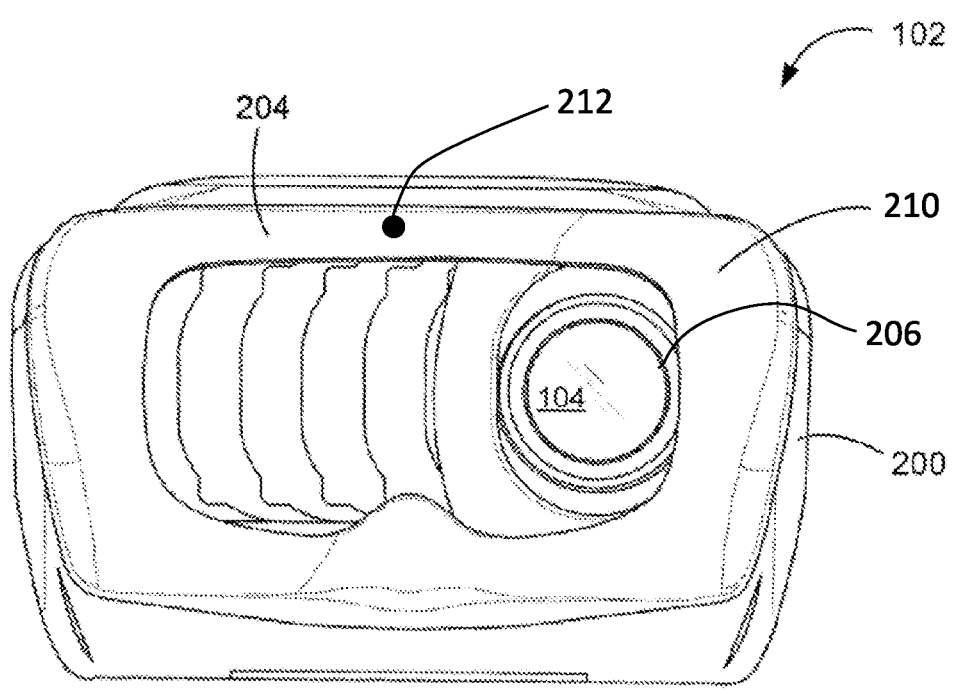
FIG. 5 is a view of the eye imaging device of FIG. 2 from the perspective of a patient during use of the device.

As shown in FIGS. 3 and 5, the housing 200 includes apertures 206 for imaging one or two eyes at a time. The camera 104 of the eye imaging device 102 is positioned within a cavity 208 formed at the end 204 of the housing 200. In certain examples, the housing 200 supports structure for raising and lowering the camera 104 to align it with the patient's P eyes. The camera 104 can be moved in three directions to accomplish imaging of both eyes of the patient P as the housing 200 is positioned against the patient P's head.

Figure 6:
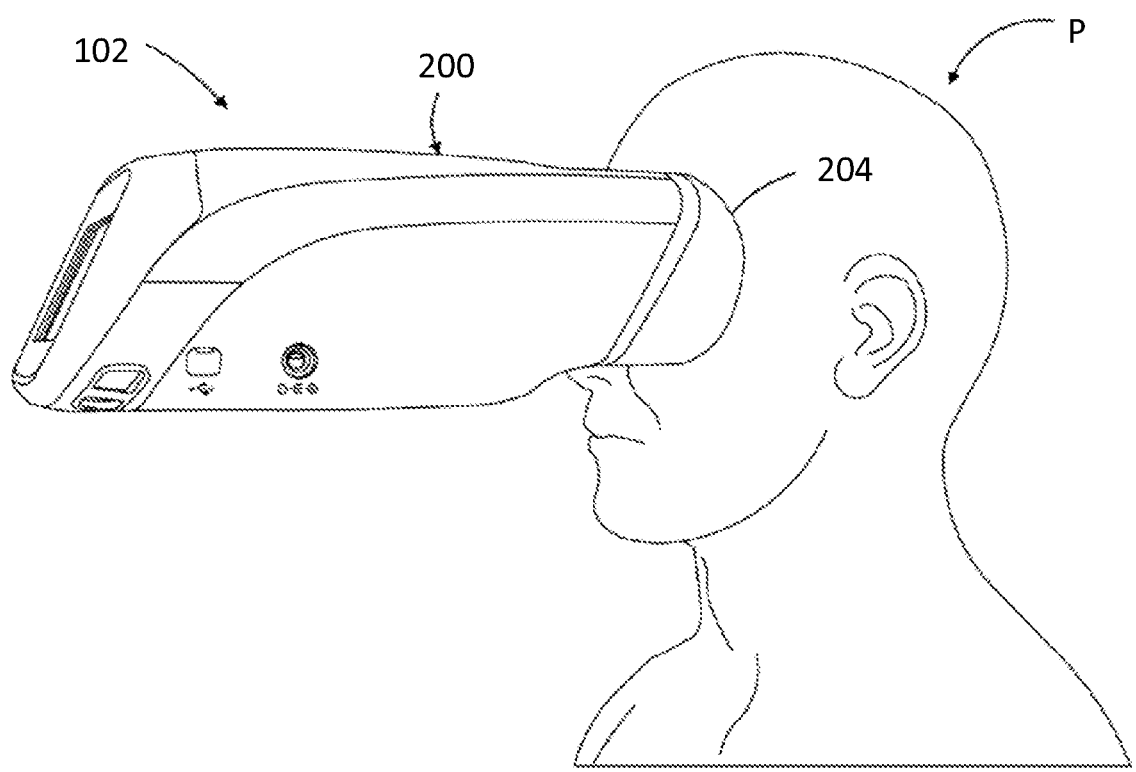
FIG. 6 is another view of the eye imaging device of FIG. 2 positioned on a patient's head and over their eyes.

The housing 200 supports positional guides for the patient P such as a surface 210 on the opposite end 204 of the housing 200 that is configured to engage the patient P's head. In certain embodiments, the housing 200 may also support additional positional guides such as an optional adjustable chin rest. The surface 210 is configured to be positioned against the patient P's head and to surround both eyes of the patient P, as shown in the example of FIG. 6. When the eye imaging device 102 is used by the patient P to capture one or more images of their eyes, such as for example without the help or assistance of the clinician C, the positional guides such as the surface 210 may help the patient P align their eyes with the one or two of the apertures 206.

In the example embodiment shown in FIGS. 2-5, the housing 200 supports the display 108. In certain embodiments, the system 100 can also use a secondary display that is part of a smart phone, tablet computer, or external monitor separately located from the housing 200 to display the at least one image captured by the camera 104.

The display 108 functions to reproduce the images produced by the eye imaging device 102 in a size and format that are readable by a clinician. For example, the display 108 can be a liquid crystal display (LCD) and active matrix organic light emitting diode (AMOLED) display. The display 108 can be touch sensitive.

The housing 200 of example eye imaging device 102 is sized to be handheld. The display 108 can display images of the eye and controls for capturing those images. In some embodiments, the display 108 is a touchscreen. In some embodiments, the housing 200 additionally supports one or more user input buttons near display 108. The display 108 and user input buttons can be used to capture one or more images of the patient P's eyes. Thus, the eye imaging device 102 is capable of being configured such that the clinician C can implement one or more automatic and/or manual workflows to capture images of the patient P's eyes.

Additionally, the eye imaging device 102 can be configured to automatically perform workflows to capture one or more images of the patient P's eyes without requiring the patient P or clinician C to use the display 108 or the one or more user input buttons near display 108 to control the operation of the eye imaging device 102. Such configuration is helpful when the eye imaging device 102 is used by the patient P without assistance from the clinician C such as when the eye imaging device 102 is used to monitor the progression of a contagious disease such as a coronavirus (e.g., COVID-19) to reduce exposure to the clinician C and other caregivers within an acute care space or a medical surgical unit of a hospital.

The eye imaging device 102 can detect when the patient's P eyes are aligned with one or two of the apertures 206 at the end 204 of the housing 200, such that the patient P is positioned and ready for the image capture sequence. In certain embodiments, the camera 104 of the eye imaging device 102 can detect when the patient P's eyes are aligned with one or two of the apertures 206. In other embodiments, a sensor 212 can be used to detect when the surface 210 is in contact or otherwise engaged with the patient P's face. In some examples, the sensor 212 can be a pressure sensor that detects when the surface 210 is pressed against the patient P's head, or can be a light sensor that detects when the patient P's face covers the sensor 212. Alternative arrangements for the sensor 212 are possible.

Figure 4:
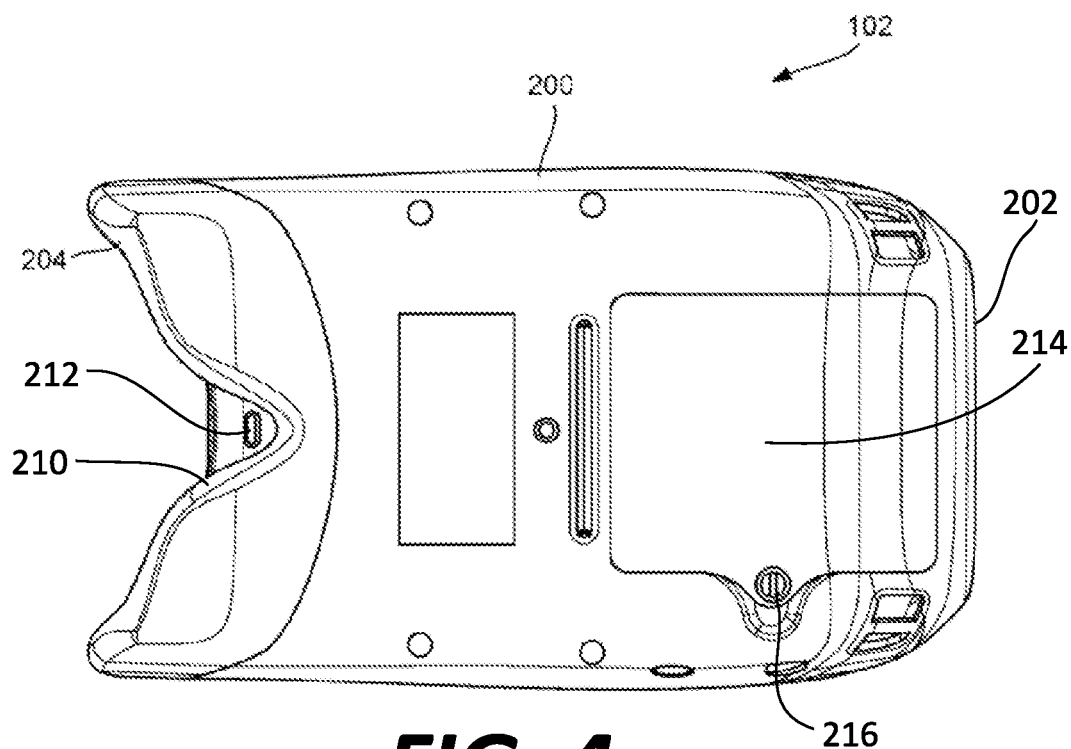
FIG. 4 is a bottom view of the eye imaging device of FIG. 2

As shown in FIG. 4, the housing 200 includes an attachment plate 214 that can be accessed by removing one or more fasteners 216. As will be described in more detail with regard to the embodiments described in FIGS. 7-10, the attachment plate 214 can be used to attach the eye imaging device 102 to another apparatus such as an articulated arm or kiosk.

Figure 7:
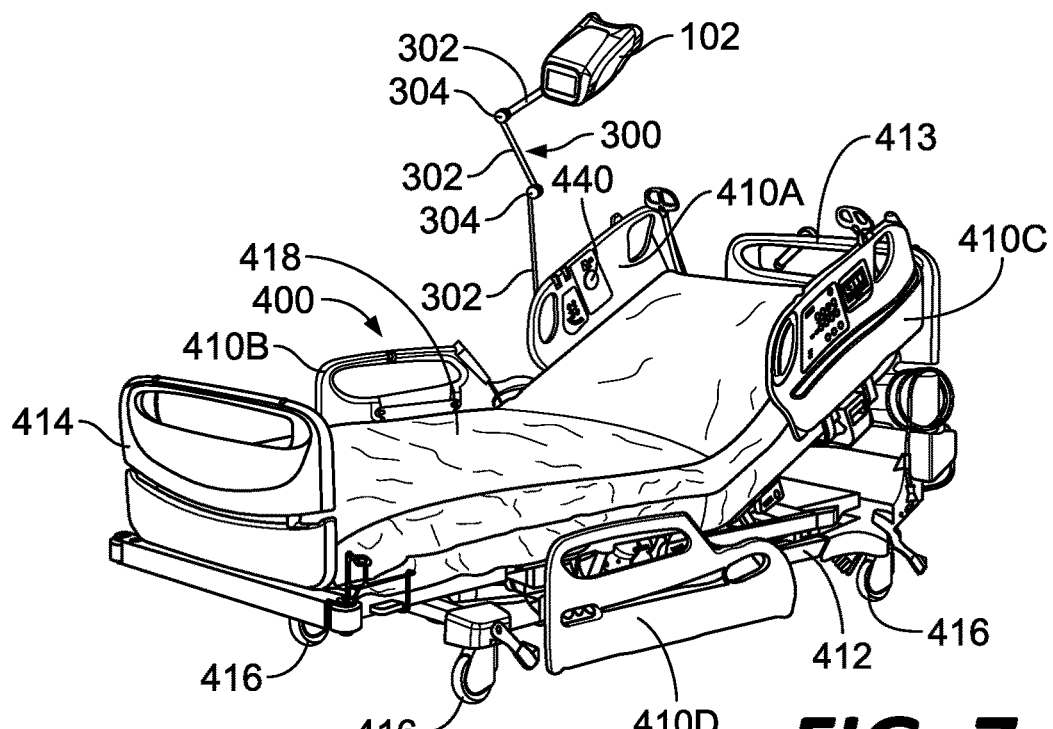
FIG. 7 illustrates the eye imaging device of FIG. 2 attached to an arm that is attached to a first type of patient support apparatus.

FIG. 7 illustrates the eye imaging device 102 attached to an arm 300, and further shows the arm 300 attached to a patient support apparatus 400 of a first type. In the example of FIG. 7, the patient support apparatus 400 is a medical surgical bed. As shown in FIG. 7, the patient support apparatus 400 includes wheels 416 such that the patient support apparatus 400 can be moved around an acute care space or medical surgical unit of a hospital. Also, the patient support apparatus 400 includes a mattress 418 supported on a frame 412 that can be adjusted between flat and inclined positions. In FIG. 7, the mattress 418 is shown in the inclined position.

The patient support apparatus 400 further includes a right siderail assembly having at least one right siderail mounted on the right side of the frame 412 and a left siderail assembly having at least one left siderail mounted on the left side of the frame 412. In this example, the right siderail assembly includes an upper right siderail 410A and a lower right siderail 410B, and the left siderail assembly includes an upper left siderail 410C and a lower left siderail 410D.

In the embodiment shown in FIG. 7, the arm 300 is attached at a first end to the upper right siderail 410A, and is attached at a second end to the eye imaging device 102. In other embodiments, the first end of the arm 300 can be attached to any of the siderails 410A-410D.

In further alternative embodiments, the first end of the arm 300 can be attached directly to the frame 412 of the patient support apparatus 400 without attachment to a siderail 410A-410D. In further embodiments, the first end of the arm 300 can be attached to a headboard 413 or a footboard 414 of the patient support apparatus 400. Additional attachment locations for the arm 300 onto the patient support apparatus 400 are possible.

Figure 8:
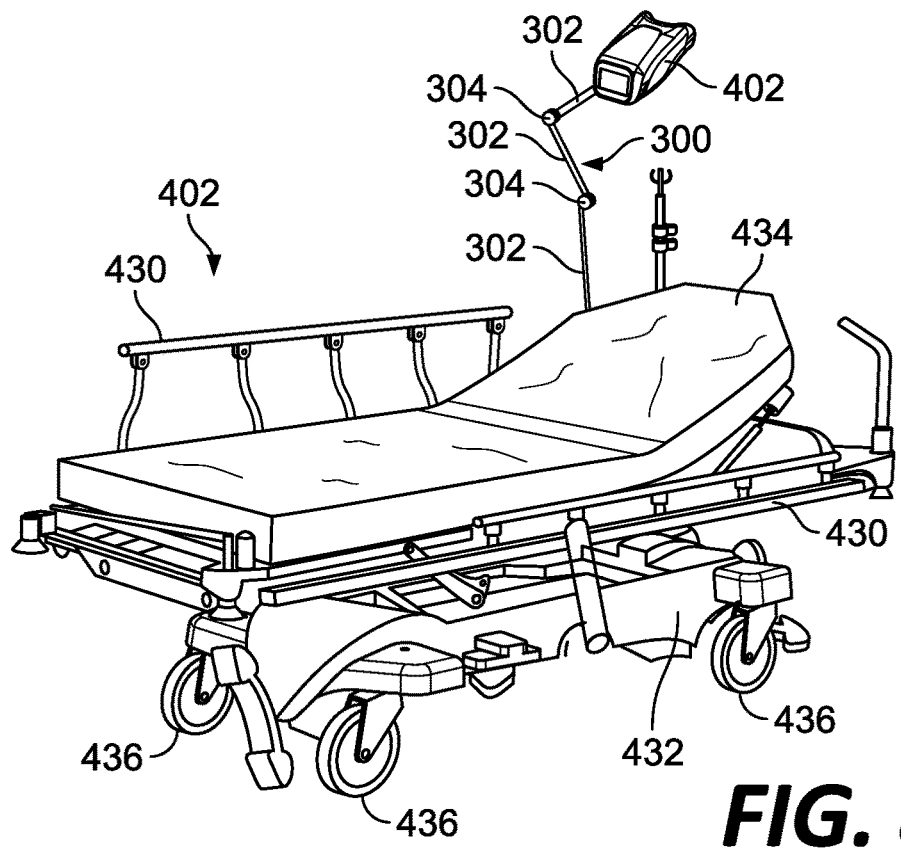
FIG. 8 illustrates the eye imaging device of FIG. 2 attached to an arm that is attached to a second type of patient support apparatus.

FIG. 8 illustrates the eye imaging device 102 attached to the arm 300, and the arm 300 is attached to a patient support apparatus 402 of a second type. In the example shown in FIG. 8, the patient support apparatus 402 is a stretcher. While the medical surgical bed and stretcher are shown and described with regard to FIGS. 7 and 8, it is possible for the eye imaging device 102 to attach, via the arm 300, to additional types of patient support apparatuses in and out of a hospital setting including, without limitation, a chair, a recliner, a table, and the like. Also, it is possible for the eye imaging device 102 to attach, via the arm 300, to additional types of structures such as a wall, and to additional types of apparatuses such as a portable or fixed stand.

Like the medical surgical bed described above with respect to FIG. 7, the patient support apparatus 402 includes one or more siderails 430 that are collapsible, and that are attached to a frame 432. The arm 300 can be attached to the siderails 430, or directly to the frame 432 without attachment to a siderail 430. The patient support apparatus 402 further includes a mattress 434 that can be adjusted between flat and inclined positions, and includes wheels 436 such that the patient support apparatus 402 can be moved around an acute care space or medical surgical unit of a hospital.

As shown in FIGS. 7 and 8, the arm 300 is attached at a second end to the housing 200 of the eye imaging device 102. In certain embodiments, the arm 300 can attach to the attachment plate 214 located on the bottom of the housing 200. Alternatively, it is possible for the arm 300 to attach to other locations on the housing 200 of the eye imaging device 102.

Figure 9:
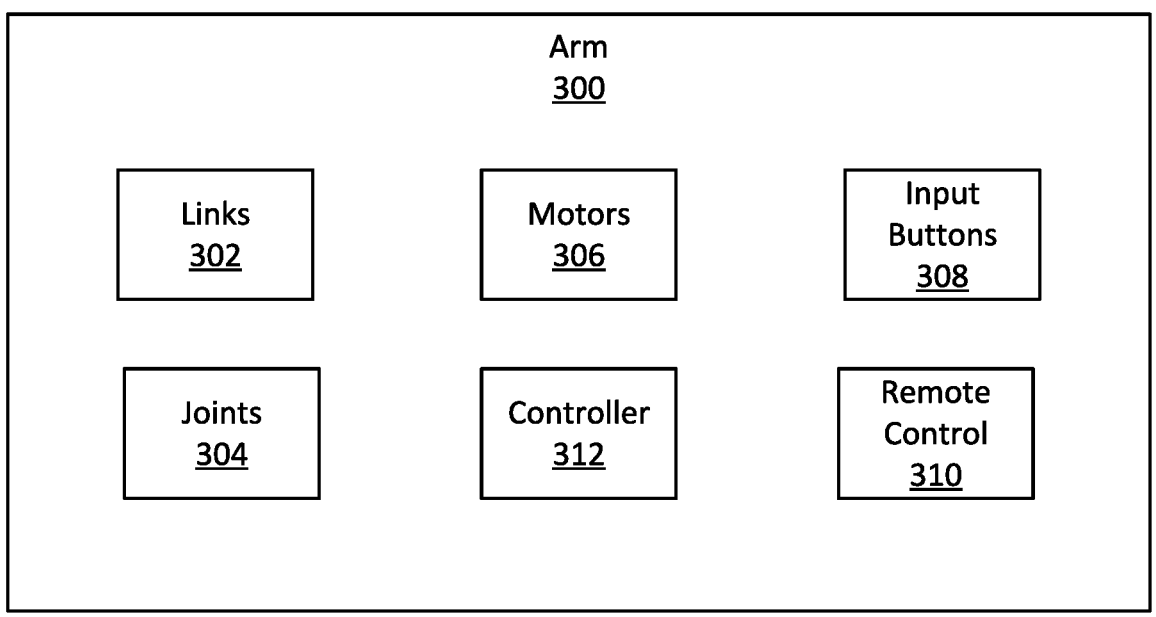
FIG. 9 schematically illustrates components of the arm of FIGS. 7 and 8 that can be used to adjust the position of the eye imaging device of FIG. 2.

FIG. 9 schematically illustrates the components of the arm 300. Referring now to FIGS. 7-9, the arm 300 includes a plurality of links 302 that are connected together by joints 304 that enable the arm 300 to move in various directions including upward, downward, left, right, forward, rearward, and any position in between. Thus, the arm 300 is an articulated arm that can be used to adjust the position of the eye imaging device 102 in a 360 degree field of motion.

The position of the eye imaging device 102 when attached to the arm 300 can be manually adjusted by the patient P while the patient P is supported on the patient support apparatus 400, 402. For example, the patient P can manually grab the housing 200 to remove it from a storage location, and can place the housing 200, and more specifically the surface 210 up against their face as shown in FIG. 6. Alternatively, or in addition to manual adjustment, the arm 300 can also be moved by one or more motors 306 that can be controlled by the patient P using one or more types of user input devices associated with the arm 300.

In certain embodiments, one or more user input buttons 308 can be positioned on the patient support apparatuses 400, 402, and can be used by the patient P to control the movement of the arm 300 using the motors 306 to adjust the position of the eye imaging device 102. For example, the user input buttons 308 can be positioned on a siderails 410, 430 of the patient support apparatus 400, 402. Alternatively, or in addition to the user input buttons 308, a remote control 310 can be provided for use by the patient P to control the movement of the arm 300 using the motors 306 to adjust the position of the eye imaging device 102.

In some further examples, the movement of the arm 300 and positioning of the eye imaging device 102 is automated by a controller 312 such that input from the patient P is not required, or is only partially required such as when the arm 300 is automated to place the eye imaging device 102 in front of the patient P's head, and all the patient P needs to do is to move the eye imaging device 102 a few inches to press the surface 210 against the patient P's head.

Figure 10:
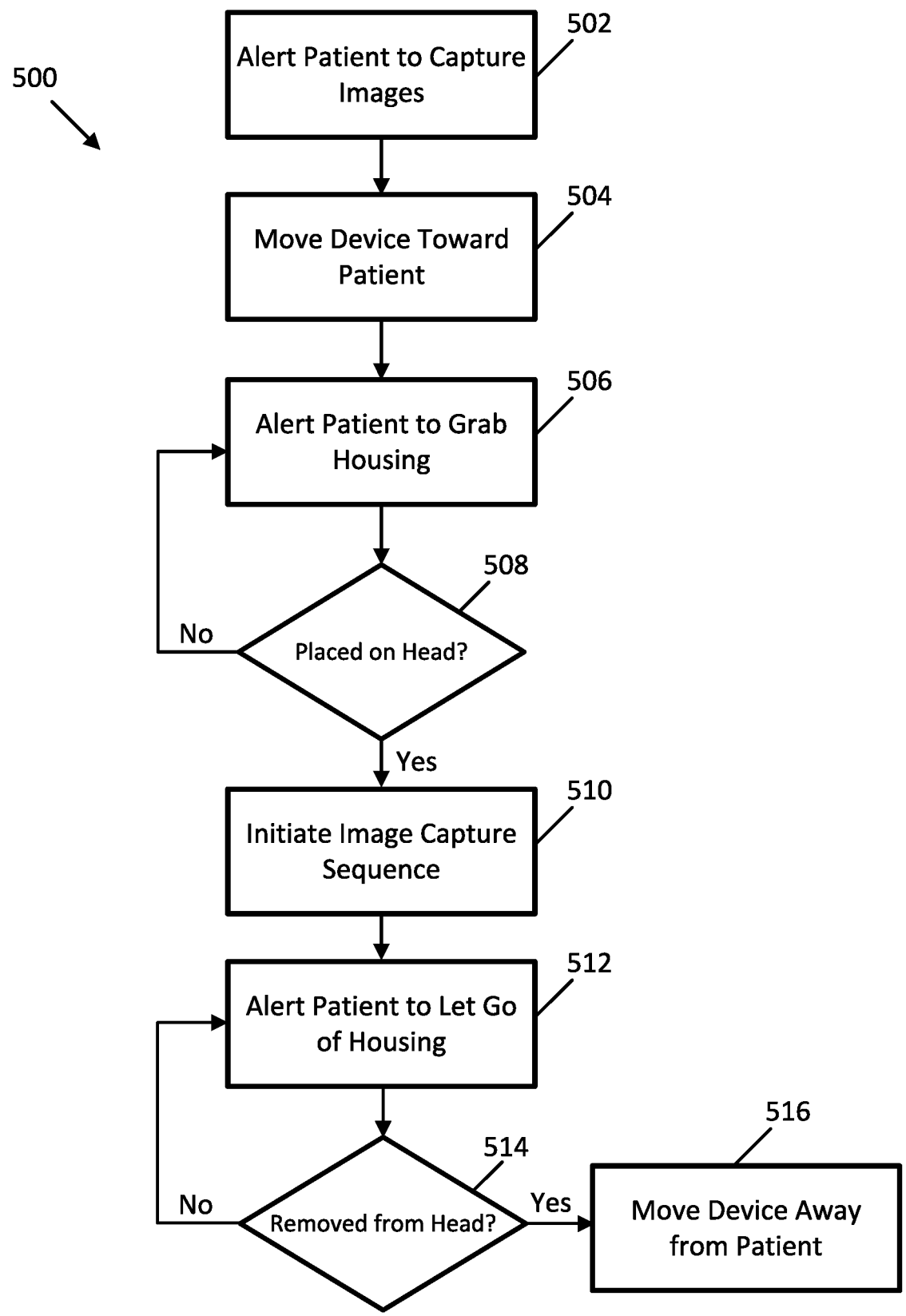
FIG. 10 illustrates a method performed by the system of FIG. 1 to capture at least one image of a patient's eyes while the patient is supported on a patient support apparatus.

FIG. 10 illustrates a method 500 of capturing at least one image of the patient P's eyes. In certain embodiments, the method 500 can be performed by the eye imaging device 102, and by using the arm 300 as shown in FIGS. 7-9. The method 500 includes an operation 502 of alerting the patient P of the need to capture one or more images of their eyes using the eye imaging device 102. The alert can be audible alert that is generated from a speaker on the patient support apparatus 400, 402 (e.g., see speaker 440 on the upper right siderail 410A in FIG. 7).

After issuing the alert, the method 500 includes an operation 504 of using the arm 300 to move the eye imaging device 102 in front of the patient P's head. In certain embodiments, the movement of the arm 300 is automated during operation 504 by the controller 312. For example, the one or more motors 306 can be controlled by the controller 312 to adjust the location of the eye imaging device 102 with respect to the patient P without requiring input from the patient.

Once the eye imaging device 102 is placed in front of the patient P's head, the method 500 includes operation 506 of alerting the patient P to grab the housing 200 and to place the eye imaging device 102 on their head, as shown in the example provided in FIG. 6. As described above, the alert can be an audible alert or any other type of notification.

Next the method 500 includes operation 508 of using the camera 104 or sensor 212 to detect that the patient P's eyes are aligned with one or two of the apertures 206 inside the cavity 208 formed at the end 204 of the housing 200. When it is detected that the patient P's eyes are not aligned with one or two of the apertures 206 (i.e., "No" in operation 508), operation 506 can be repeated to instruct the patient P to place the eye imaging device 102 on their head.

Next, the method 500 includes an operation 510 of automatically capturing one or more images of the patient P's eyes when the camera 104 or sensor 212 detect that the patient P's eyes are aligned with the apertures 206 (i.e., "Yes" in operation 508). Advantageously, the images are captured without requiring any input from the patient P such that the patient P does not need to operate the display 108 or any user input buttons near display 108 to capture the one or more images of their eyes. Thus, the use of the eye imaging device 102 by the patient P is made easier, especially when the clinician C is unavailable to assist the patient P.

After completion of the image capture sequence, the method 500 can include an operation 512 of sending another alert to notify the patient P that the image capture sequence is complete, and to remove the eye imaging device 102 from their head. As described above, the alert can be an audible alert or any other types of notification including a notification displayed inside the cavity 208 formed at the end 204 of the housing 200 that can be viewed by the patient P while the eye imaging device 102 remains placed on the patient P's head.

Next, the method 500 can include an operation 514 of using the camera 104 or sensor 212 to detect whether the eye imaging device 102 is removed from the patient P's head. When the camera 104 or sensor 212 detects that the eye imaging device 102 has not been removed from the patient P's head (i.e., "No" in operation 514), operation 512 can be repeated to issue another alert to instruct the patient P to remove the eye imaging device 102 from their head.

Thereafter, the method 500 includes operation 516 of using the arm 300 to move the eye imaging device 102 away from the patient P's head, and to move the eye imaging device 102 to a storage location that does not interfere with the patient P while the patient P remains supported on the patient support apparatus 400, 402. For example, the arm 300 can stow the eye imaging device 102 inside the frame 412, 432, or behind a siderail 410, 430 of the patient support apparatus 400, 402 such that it does not get in the way of the patient P when it is not being used. In operation 516, the movement of the arm 300 can be automated such that the one or more motors 306 are controlled by the controller 312 to automatically adjust the location of the eye imaging device 102 with respect to the patient P without requiring input from the patient.

In certain embodiments, additional diagnostic devices may be attached to the arm 300. For example, certain diagnostic devices may require precise placement relative to the patient P, and the arm 300 can automate the movement of these devices to position them in the correct placement. Additional diagnostic devices that may be used with the arm 300 include devices used to record heart and lung sounds, and to record images the patient P's throat.

While the method 500 is described above as being performed without assistance from the clinician C, it is contemplated that in certain embodiments, the clinician C may assist the patient P in placing the eye imaging device 102 on their head. This may especially occur for patients who are too weak or deteriorated to grab and move the eye imaging device 102 even when the arm 300 is used to place the eye imaging device 102 in front of them.

Figure 11:
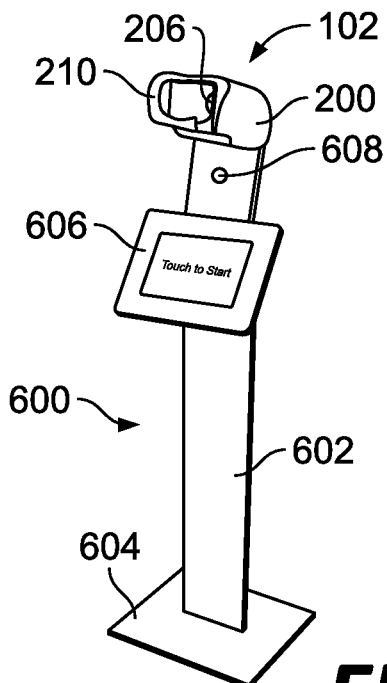
FIG. 11 illustrates the eye imaging device of FIG. 2 attached to a first type of kiosk with a digital display.

FIG. 11 illustrates the eye imaging device 102 attached to a kiosk 600 of a first type. In the example shown in FIG. 11, the kiosk 600 is a standalone kiosk that can be placed within a hospital such as in an emergency room where the eye imaging device 102 can be used for disease risk assessment such as for sepsis or coronavirus. It is contemplated that the kiosk 600 may be used in additional medical settings such as in a primary care physician's office, a health clinic, pharmacy, long term care facility, nursing home, and the like. Additionally, the kiosk 600 may be used in non-medical settings such as in the lobby of an office building or an airport terminal.

As shown in FIG. 11, the eye imaging device 102 is attached to a pedestal 602 that includes a base 604. In certain embodiments, the eye imaging device 102 is fixed to the pedestal such that it cannot be removed from the pedestal. In certain embodiments, the height of the pedestal 602 can be adjusted to accommodate users of various heights. In alternative examples, the eye imaging device 102 can be removably attached to the pedestal 602 such that it can be picked up by the user and placed on the user's head for disease risk assessment, and then returned to the pedestal 602 after completion of the disease risk assessment. In certain embodiments, the eye imaging device 102 can be tethered to the pedestal to prevent theft of the system. In some embodiments, a power source of the eye imaging device 102 is recharged while the eye imaging device 102 is mounted and/or docked on the pedestal 602.

The kiosk 600 includes a digital display 606 that is also attached to the pedestal 602. The digital display 606 can be used to display instructions for a user to perform a method for disease risk assessment that uses the eye imaging device 102. In certain embodiments, the method for disease risk assessment is the method 1300 which is described in more detail below with reference to FIG. 13. In certain embodiments, one or more speakers 608 may be embedded in the pedestal 602 or may be included with the digital display 606 to provide audio instructions for the user. The digital display 606 can display a disease risk assessment based on one or more abnormalities that may be detected by the eye imaging device 102.

The digital display 606 is a touchscreen that can be used by a user to enter additional information that can be used to calculate a risk score. For example, the user can use the digital display 606 to enter data such as their height, weight, body mass index (BMI), comorbidities, age, symptoms, exposure to contagious disease (e.g., COVID-19), and other similar data.

Figure 12:
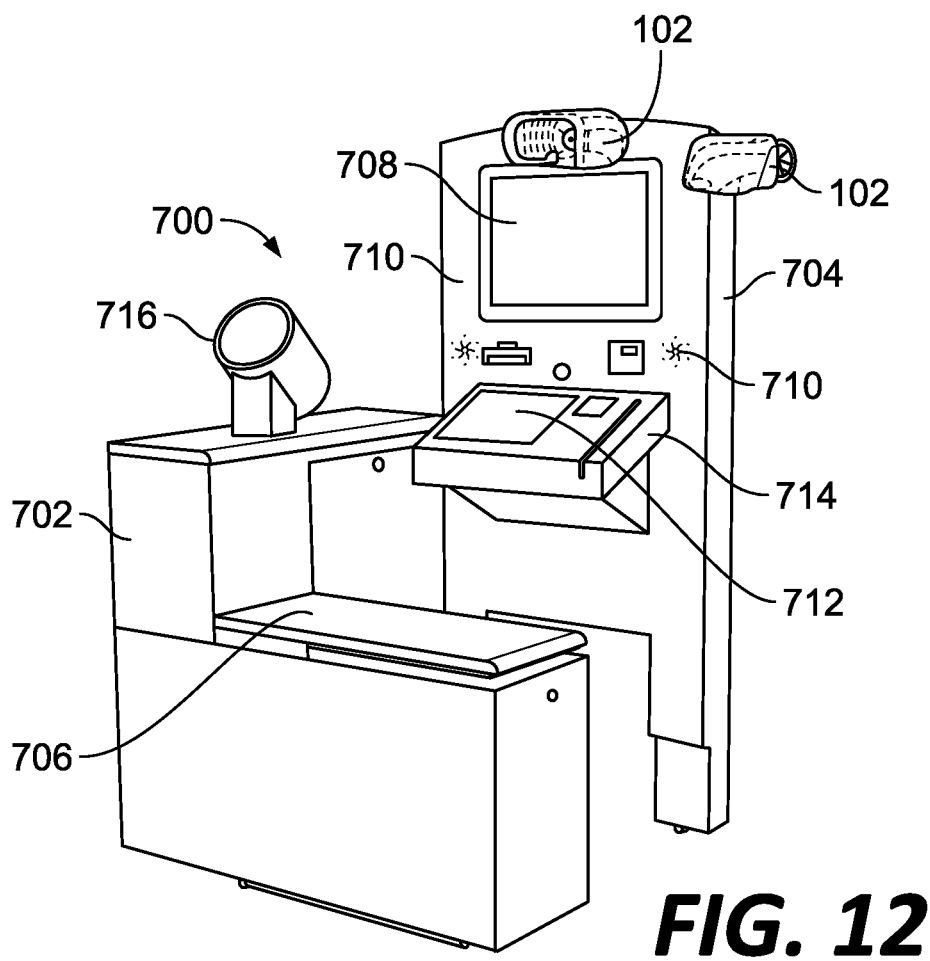
FIG. 12 illustrates the eye imaging device of FIG. 2 attached to a second type of kiosk with a digital display.

FIG. 12 illustrates the eye imaging device of 102 attached to a kiosk 700 of a second type. In the example shown in FIG. 12, the kiosk 700 is an integrated kiosk that may include a plurality of devices 716 for measuring the vital signs of a user and to provide an enhanced disease risk assessment. The devices 716 may include devices to measure the temperature, SpO2, blood pressure, heart rate, and respiration rate of the user.

Like the kiosk 600 described above, the kiosk 700 can be placed within a hospital such as in an emergency room where the eye imaging device 102 can be used for disease risk assessment such as for sepsis or coronavirus. It is contemplated that the kiosk 700 may be used in additional medical settings such as in a primary care physician's office, a health clinic, pharmacy, long term care facility, nursing home, and the like. The kiosk 700 may also be used in non-medical settings such as in the lobby of an office building or an airport terminal.

The kiosk 700 may include a cubicle like structure 702 that includes a wall 704 that can provide privacy for the user, and may include a bench 706 for the user to sit on. Like, the kiosk 600 described above, the kiosk 700 includes a digital display 708 that can be used to display instructions that require the user to use the eye imaging device 102 to perform a method for disease risk assessment. Also, one or more speakers 710 may be embedded in the cubicle like structure 702 or may be included with the digital display 708 to provide audio instructions for the user. The digital display 708 can display a disease risk assessment based on one or more abnormalities that may be detected by the eye imaging device 102.

The kiosk 700 may include one or more input devices 712 mounted to a counter 714 that is attached to the wall 704. In certain examples, the one or more input devices 712 include a touchscreen. A user can use the one or more input devices 712 to enter additional information that can be used to calculate a risk score. For example, the user can use the one or more input devices 712 to enter data such as their height, weight, body mass index (BMI), comorbidities, age, symptoms, exposure to contagious disease (e.g., COVID-19), and other similar data.

As shown in FIG. 12, a plurality of eye imaging devices 102 may be mounted to the cubicle like structure 702. In this embodiment, a user can remove the eye imaging device 102 from the wall 704 and can place it on their head. When an image capture sequence is completed, the user can return the eye imaging device 102 to the wall 704 for storage. In certain embodiments, the eye imaging device 102 can be tethered to the wall 704 to prevent theft of the system. In some embodiments, a power source of the eye imaging device 102 is recharged while the eye imaging device 102 is mounted and/or docked on the wall 704.

Figure 13:
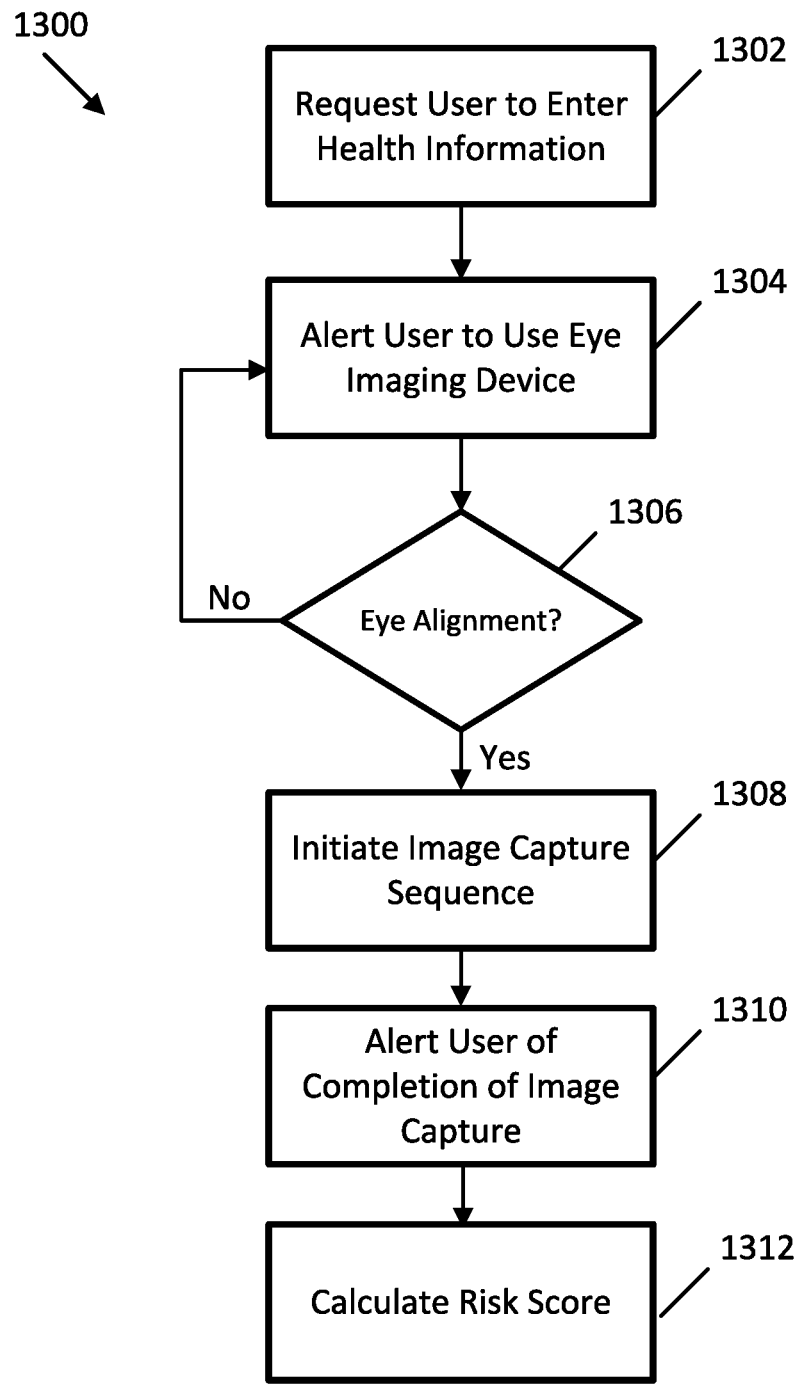
FIG. 13 illustrates a method of disease risk assessment that can be implemented by the kiosks of FIGS. 11 and 12.

FIG. 13 illustrates a method 1300 of disease risk assessment that can be implemented by the kiosks 600, 700. The method 1300 can include an operation 1302 of requesting a user to enter health information using the digital display 606 in the case of the kiosk 600 or the one or more input devices 712 in the case of the kiosk 700. The health information entered by the user may include, without limitation, the user's height, weight, body mass index (BMI), comorbidities, age, symptoms, exposure to contagious disease (e.g., COVID-19), and other relevant data that may be useful in determining a risk score for deterioration from a disease. In the embodiment of the kiosk 700, one or more devices 716 may be used to obtain vital signs data including the temperature, SpO2, blood pressure, heart rate, and respiration rate of the user.

Next, the method 1300 includes an operation 1304 of alerting the user to use the eye imaging device 102 to capture one or more images of their eyes. The alert can be displayed on the digital displays 606, 708 or can be an audible alert generated from one or more speaker 608, 710 of the kiosks 600, 700. Additional types of alerts are possible.

In the example kiosk 600, the alert can simply request the user to press their face into the eye imaging device 102. In embodiments where the height of the pedestal 602 is adjustable, the alert can instruct the user to adjust the height of the pedestal 602 so that the eye imaging device 102 is level with their head, and thereafter press their face into the surface 210 of the eye imaging device 102. In embodiments where the eye imaging device 102 is removably attached to the pedestal 602, the alert can request the user to remove the eye imaging device 102 from the pedestal 602 and to place the eye imaging device 102 on their head.

In the example kiosk 700, the alert can instruct the user to remove the eye imaging device 102 from the wall 704 and to place it on their head. In embodiments where the eye imaging device 102 is fixed to the wall 704 of the kiosk 700, the alert can simply request the user to press their face against the surface 210 of the eye imaging device 102.

Next the method 1300 includes operation 1306 of using the camera 104 or sensor 212 to detect whether the user's eyes are aligned with the apertures 206. When the camera 104 or sensor 212 does not detect that the user's eyes are aligned with the apertures 206 (i.e., "No" in operation 1306), the method 1300 repeats the operation 1304 to issue another alert that instructs the user to properly place the eye imaging device 102 on their head.

When the camera 104 or sensor 212 detects that the user's eyes are aligned with the apertures 206 (i.e., "Yes" in operation 1306), the method 1300 proceeds to an operation 1308 of capturing at least one image. The at least one image is automatically captured without requiring any input from the user such that the user does not need to operate the display 108 or any user input buttons near display 108 of the eye imaging device 102 to capture the image. This makes use of the eye imaging device 102 easier for the user.

After completion of the image capture sequence, the method 1300 includes an operation 1310 of sending another alert to notify the user that the image capture sequence is complete, and to release their head from contacting the surface 210 of the eye imaging device 102. In certain embodiments, the alert is audible. Alternatively, or in combination with an audible alert, a notification can be displayed inside the cavity 208 that can be viewed by the user while the user's face is pressed against the surface 210 of the eye imaging device 102.

Thereafter, the method 1300 includes an operation 1312 of calculating a risk score based on the information entered into the digital displays 606, 708 at operation 1302, and one or more abnormalities detected from image capture sequence performed at operation 1308. In some embodiments, the risk score is displayed on the digital displays 606, 708. In certain embodiments, in addition to displaying the risk score, the method 1300 may also display a referral for the user based on the risk score such as to seek immediate medical attention.

Figure 14:
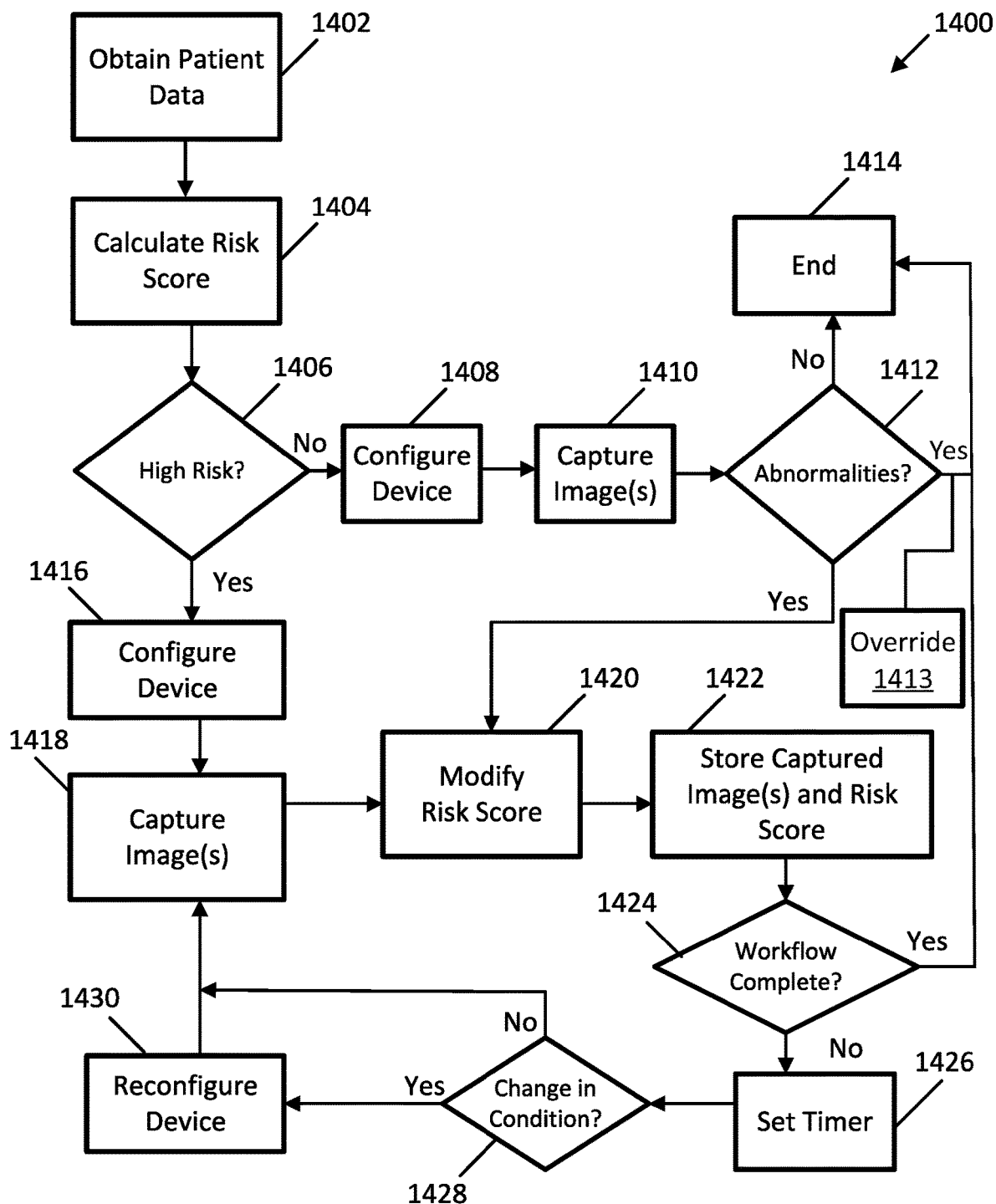
FIG. 14 illustrates a method of using the eye imaging device of FIG. 2 to take at least one image of a patient's eyes.

FIG. 14 illustrates a method 1400 of using eye imaging device 102 to take one or more images of the patient P's eyes. The method 1400 can be performed in embodiments where the eye imaging device 102 is attached to the arm 300, and the arm 300 is attached to a patient support apparatus 400, 402 such as those shown in FIGS. 7 and 8. Additionally, the method 1400 can be performed in embodiments where the eye imaging device 102 is part of a kiosk such as the kiosks 600, 700 that are shown in FIGS. 11 and 12.

The method 1400 includes an initial operation 1402 of obtaining patient data. The patient data can include age, comorbidities, symptoms, complaints, lab results, prior vital signs readings, and the like. The patient data can be obtained directly from a patient such as in response to a questionnaire that allows the patient or a clinician to enter the patient data through a user input device. Alternatively, the patient data can be acquired from an Electronic Medical Record (EMR) of the patient when the identity of the patient is known.

Next, the method 1400 includes an operation 1404 of calculating an initial risk score for the patient based on the obtained patient data. The risk score represents a risk that the patient will experience a severe deterioration from a disease. A high risk score indicates that the patient P will likely experience a severe deterioration from the disease. A low risk score indicates that the patient P will not likely experience a severe deterioration from the disease.

In certain embodiments, the risk score is calculated for a virus such as COVID-19. In such embodiments, the risk score increases with age and comorbidities including, without limitation, cancer, chronic kidney disease, chronic obstructive pulmonary disease (COPD), immunocompromised state (i.e., weakened immune system), obesity (e.g., body mass index (BMI) of 30 or higher), serious heart conditions such as heart failure, coronary artery disease, or cardiomyopathies, sickle cell disease, and type 2 diabetes. Additionally, the risk score for COVID-19 may also increase with asthma (moderate-to-severe), cerebrovascular disease that affects blood vessels and bloody supply to the brain, cystic fibrosis, hypertension or high blood pressure, neurological conditions such as dementia, liver disease, pregnancy, pulmonary fibrosis (e.g., having damaged or scarred lung tissues), smoking, thalassemia, and type 1 diabetes.

In certain embodiments, the risk score is calculated for sepsis. In such embodiments, the risk score is based on age and comorbidities including, without limitation, pregnancy, weakened immune system, chronic conditions such as diabetes, lung, kidney, liver diseases, dementia, and cancer, prior hospitalizations, use of indwelling prosthetic devices such as catheters, heart valves, vascular bypass grafts, ocular lenses, artificial joints, and central nervous shunts, and malnutrition. Aspects for identifying sepsis risk and monitoring sepsis progression are described in U.S. patent application Ser. No. 16/832,672 filed on Mar. 27, 2020, U.S. patent application Ser. No. 16/847,729 filed on Apr. 14, 2020, and U.S. patent application No. 62/893,985 filed on Aug. 30, 2019, all of which are hereby incorporated by reference in their entirety.

In certain embodiments, the eye imaging device 102 automatically calculates the risk score based on the obtained patient data. In alternative examples, the eye imaging device 102 can receive the calculated risk score from another device that can transfer the calculated risk score to the eye imaging device 102 through the network 110. In some further embodiments, the eye imaging device 102 can receive the calculated risk score from a user who enters the risk score using the display 108 or one or more user input buttons near display 108.

Next, the method 1400 includes an operation 1406 of determining whether the risk score is high or low. When the risk score is low (i.e., "No" at operation 1406) the method 1400 proceeds to an operation 1408 of configuring the eye imaging device 102 to perform a first type of workflow. When the risk score is high (i.e., "Yes" at operation 1406) the method 1400 proceeds to an operation 1416 of configuring the eye imaging device 102 to perform a second type of workflow. In some embodiments, the risk score is a numerical value and the decision at operation 1406 is determined by comparing the risk score to a threshold value such that when the risk score is less than the threshold value, the risk score is determined to be low, and when the risk score exceeds the threshold value, the risk score is determined to be high.

The first type of workflow can be less complex than the second type of workflow. For example, the first type of workflow can include capturing a single image, whereas the second type of workflow can include capturing a plurality of images under different lighting conditions, filters, diopters, and the like. Each of the plurality of images from the second type of workflow may highlight different characteristics of the patient P's eyes for analysis.

As shown in FIG. 14, after the eye imaging device 102 is configured at operation 1408 to perform the first type of workflow, the method 1400 proceeds to an operation 1410 of capturing at least one image under the first type of workflow. Similarly, after the eye imaging device 102 is configured at operation 1416 to perform the second type of workflow, the method 1400 proceeds to an operation 1418 of capturing at least one image under the second type of workflow. As described above, the first and second types of workflows can be initiated when the camera 104 or sensor 212 detect that the patient's eyes are aligned with one or two of the apertures 206 inside the cavity 208 of the housing 200 of the eye imaging device 102. Thus, the eye imaging device 102 can capture the at least one image under the first and second types of workflows without requiring the patient or a clinician to use the display 108 or the one or more user input buttons near display 108 to control the operation of the eye imaging device 102.

In certain embodiments, the eye imaging device 102 is connected to one or more systems via the network 110 that can identify the proper person allowed to use the eye imaging device 102 for capturing the at least one image. For example, access may be granted to certain persons such as the patient or a clinician assigned to the patient, while access may be denied for certain persons such as clinicians who are not assigned to the patient.

After completion of operation 1410, the method 1400 proceeds to an operation 1412 of analyzing the at least one image captured under the first type of workflow to determine whether there are any abnormalities. When no abnormalities are detected (i.e., "No" at operation 1412), the method 1400 terminates at operation 1414. When one or more abnormalities are detected (i.e., "Yes" at operation 1412), the method 1400 proceeds to operation 1420 of modifying the risk score based the one or more detected abnormalities. For example, the one or more detected abnormalities can increase the risk score. In certain embodiments, when one or more abnormalities are detected (i.e., "Yes" at operation 1412), the method 1400 may include presenting a manual override 1413 such that the method 1400 does not automatically proceed to operation 1420, and instead can terminate at operation 1414 when a clinician determines that they have sufficient information such that further analysis is not needed.

After completion of operation 1418, the method 1400 similarly proceeds to the operation 1420 of modifying the risk score based on data obtained from the at least one image captured under the second type of workflow. The data obtained from the at least one image captured under the second type of workflow can increase or decrease the risk score for patient deterioration. For example, when one or more abnormalities are detected from the at least one image captured under the second type of workflow, the risk score can be increased at operation 1420. Alternatively, when no abnormalities are detected from the at least one image captured under the second type of workflow, the risk score can be decreased at operation 1420.

Accordingly, the risk score determined at operation 1420 is an enhanced risk score that takes into consideration microvascular assessment from the at least one image captured under the first or second workflows. Advantageously, by adjusting the risk score to take into consideration the microvascular assessment, the enhanced risk score is more accurate in predicting patient deterioration from diseases that may affect the microvasculature. As described above, diseases that may affect the microvasculature include sepsis and COVID-19.

Next, the method 1400 proceeds to an operation 1422 of storing the enhanced risk score and the at least one image captured under the first or second types of workflow in a memory where it can be accessed by a clinician for further analysis. The memory can be on the eye imaging device 102 itself, or the memory can be remotely located from the eye imaging device 102 such as on a cloud network. The eye imaging device 102 is connected to one or more systems via the network 110 that can identify the proper person allowed to access the enhanced risk score and at least one image. For example, access may be granted to certain persons such as the patient or a clinician assigned to the patient, while access may be denied for certain persons such as clinicians who are not assigned to the patient.

Alternatively, or in addition to storing the enhanced risk score and at least one image, operation 1422 may also include sending the enhanced risk score and at least one image directly to a clinician for further analysis. In this example, the network 110 can be used to send the at least one image to the clinician, and one or more systems connected to the network 110 can be used identify the correct clinician to send the enhanced risk score and at least one image.

Next, the method 1400 proceeds to an operation 1424 of determining whether the workflows are complete. When the workflows are complete (i.e., "Yes" at operation 1424), the method 1400 ends at operation 1414. When the workflows are not complete (i.e., "No" at operation 1424), the method 1400 proceeds to an operation 1424 of setting or resetting the timer 112 (see FIG. 1) of the eye imaging device 102 based on the enhanced risk score.

As described above, the timer 112 can be used to let the clinician or the patient know when an image or set of images should be taken by the eye imaging device 102. For example, the timer 112 after a predetermined period of time has expired can trigger an alert to be generated to remind the clinician or patient to take additional images using the eye imaging device 102. The alert can be generated on the eye imaging device 102 such as a flashing light or an audio instruction, or in other instances, the alert can be generated on another device such as a patient support apparatus 400, 402 (see FIGS. 7 and 8), or on another device associated with the clinician or patient such as a smartphone, tablet computer, and the like.

As an illustrative example, when the enhanced risk score is high, the timer 112 can be set to have a shorter interval of timer such that the alert will be generated more frequently. When the enhanced risk score is low, the timer 112 can be set have a longer interval of time such that the alert will be generated less frequently. Additionally, when the enhanced risk score increases from a previously calculated risk score, the interval of time set by the timer 112 for the alert can be shortened. Alternatively, when the enhanced risk score decreases from a previously calculated risk score, the interval of time set by the timer 112 for the alert can be lengthened. In certain embodiments, the timer 112 is automated by the computing device 1500 such that the time interval for the alert triggered by the timer 112 is automatically adjusted without any input from the clinician or patient, and is instead automatically updated based on the enhanced risk.

Next, the method 1400 proceeds to an operation 1428 of determining whether the condition of the patient P has changed such as whether the patient's condition has improved or deteriorated. In certain embodiments, the change in the patient's condition is determined from data obtained from the at least one image captured at operations 1410, 1418. Alternatively, or in addition to the data obtained from the at least one image captured at operations 1410, 1418, the change in the condition of the patient can be determined from updated vital signs measurements taken during performance of the method 1400 or other observations of the patient.

When the condition of the patient P is determined as not having changed (i.e., "No" at operation 1428), the method 1400 proceeds to capture additional images under the same workflow that was used to capture the images under operations 1410, 1418. When the condition of the patient P is determined as having changed (i.e., "Yes" at operation 1428), the method 1400 proceeds to an operation 1430 of reconfiguring the eye imaging device 102 to perform another type of workflow based on the changed condition that is different from the first and second types of workflows that are described above.

As an illustrative example, when the patient's condition is improving, the eye imaging device 102 can be reconfigured to perform another type of workflow that is less complex such that it captures fewer images, or less detailed images. As another illustrative example, when the patient's condition is deteriorating, the eye imaging device 102 can be reconfigured to perform another type of workflow that is more complex such that it captures a greater number of images, or images that are more detailed.

In some embodiments, the eye imaging device 102 is reconfigured at operation 1430 regardless of detected changes in the patient's condition. In such embodiments, fewer images or image types are captured to monitor the progress of that patient because fewer images or image types may be needed as the condition of the patient remains steady.

The method 1400 may repeat the operations 1418-1430 as many times as needed until the workflows are complete (i.e., "Yes" at operation 1424). Each time the operations 1418-1430 are repeated, the eye imaging device 102 may automatically adjust the type of image or images it takes based on the reconfiguration performed at operation 1430. For instance, in a first pass through operations 1418-1430, a sequence of images providing a rich set of data are acquired at operation 1418, and each time the operations 1418-1430 are repeated, fewer images or fewer image types are acquired at operation 1418 as the condition of the patient progresses.

Additionally, repetition of operation 1420 provides a trend of enhanced risk scores based on updated microvascular assessments from the images acquired from the eye imaging device 102. The trended risk scores can indicate the patient's progress. Furthermore, repetition of operation 1422 can provide the clinician with continuous updates of the enhanced risk score.

The method 1400 can improve the use of the eye imaging device 102 in an acute care space or medical surgical unit by notifying a user when they should be taking an image or set of images with the eye imaging device 102 by using of the timer 112 to generate an alert. Also, the method 1400 can provide earlier detection of patient deterioration from diseases such as COVID-19 and sepsis by continuously monitoring microvascular changes in the patient's eyes.

FIG. 15 schematically illustrates an example computing device 1500 which can be used to implement aspects of the present disclosure, such as the functions of the eye imaging device 102 and server 114 described above. The computing device 1500 includes a processing unit 1502, a system memory 1508, and a system bus 1520 that couples the system memory 1508 to the processing unit 1502. In certain embodiments, the processing unit 1502 is the image processor 106 of the eye imaging device 102 of FIG. 1. The processing unit 1502 is an example of a processing device such as a central processing unit (CPU). The system memory 1508 includes a random-access memory ("RAM") 1510 and a read-only memory ("ROM") 1512. A basic input/output logic containing the basic routines that help to transfer information between elements within the computing device 1500, such as during startup, is stored in the ROM 1512.

The computing device 1500 can also include a mass storage device 1514 that is able to store software instructions and data. The mass storage device 1514 is connected to the processing unit 1502 through a mass storage controller (not shown) connected to the system bus 1520. The mass storage device 1514 and its associated computer-readable data storage media provide non-volatile, non-transitory storage for the computing device 1500.

Although the description of computer-readable data storage media contained herein refers to a mass storage device, it should be appreciated by those skilled in the art that computer-readable data storage media can be any available non-transitory, physical device or article of manufacture from which the device can read data and/or instructions. The mass storage device 1514 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, or any other medium which can be used to store information, and which can be accessed by the device.

The computing device 1500 may operate in a networked environment using logical connections to remote network devices, including the server 114, through the network 110, such as a local network, the Internet, or another type of network. The computing device 1500 connects to the network 110 through a network interface unit 1504 connected to the system bus 1520. The network interface unit 1504 may also be utilized to connect to other types of networks and remote computing systems.

The computing device 1500 can also include an input/output controller 1506 for receiving and processing input from a number of input devices. Similarly, the input/output controller 1506 may provide output to a number of output devices.

The mass storage device 1514 and the RAM 1510 can store software instructions and data. The software instructions can include an operating system 1518 suitable for controlling the operation of the device. The mass storage device 1514 and/or the RAM 1510 also store software instructions 1516, that when executed by the processing unit 1502, cause the device to provide the functionality of the device discussed in this document.

The various embodiments described above are provided by way of illustration only and should not be construed to be limiting in any way. Various modifications can be made to the embodiments described above without departing from the true spirit and scope of the disclosure.

What is claimed is:

1. A system for capturing one or more eye images, the system comprising:
   an eye imaging device having a camera configured to capture the eye images; and
   a computing device having at least one processor, and a memory storing instructions which, when executed by the at least one processor, cause the system to:
      determine a workflow for capturing the eye images using the eye imaging device, the workflow determined based on a risk score for a given patient, wherein the risk score represents a likelihood of deterioration from a disease affecting macro vital signs;
      perform the workflow on the eye imaging device to capture the eye images;
      conduct a microvascular assessment based on the captured eye images; and
      adjust the risk score based on the microvascular assessment to generate an enhanced risk score; and
      set a timer to trigger an alert to take additional eye images using the eye imaging device, wherein the timer is set based on the enhanced risk score.

2. The system of claim 1, wherein the memory stores further instructions which, when executed by the at least one processor, cause the system to:
   adjust the workflow on the eye imaging device based on the microvascular assessment.

3. The system of claim 2, wherein the workflow on the eye imaging device is adjusted to capture different quantities and types of eye images.

4. The system of claim 1, wherein the memory stores further instructions which, when executed by the at least one processor, cause the system to:
   adjust the workflow on the eye imaging device based on a disease progress.

5. The system of claim 1, wherein the workflow performed on the eye imaging device captures a single image of a predetermined type based on the risk score for the patient.

6. The system of claim 1, wherein the workflow performed on the eye imaging device captures a predetermined sequence of images for conducting the microvascular assessment.

7. The system of claim 1, wherein the eye imaging device is attached to an arm that is controllable to adjust the position of the eye imaging device relative to the patient, and wherein the arm is an articulated arm that includes one or more motors that are controlled by the computing device to position the eye imaging device in front of the patient.

8. The system of claim 1, wherein the eye imaging device is mounted to a kiosk that includes a digital display, and wherein the digital display is configured to output instructions for the patient to perform a disease risk assessment that uses the eye imaging device.

9. The system of claim 1, wherein the computing device is part of the eye imaging device or is part of a server remotely located from the eye imaging device.

10. A method for capturing one or more eye images, the method comprising:
- determining a workflow for capturing the one or more eye images using an eye imaging device, the workflow determined based on a risk score for a given patient, wherein the risk score represents a likelihood of deterioration from a disease affecting macro vital signs;
- performing the workflow on the eye imaging device to capture the eye images;
- conducting a microvascular assessment based on the captured eye images; and
- adjusting the risk score based on the microvascular assessment to generate an enhanced risk score; and
- setting a timer to trigger an alert to take additional eye images using the eye imaging device, wherein the timer is set based on the enhanced risk score.

11. The method of claim 10, further comprising:
- adjusting the workflow on the eye imaging device based on the microvascular assessment.

12. The method of claim 11, wherein the workflow on the eye imaging device is adjusted to capture different quantities and types of eye images.

13. The method of claim 10, further comprising:
- adjusting the workflow on the eye imaging device based on a disease progress.

14. A non-transitory computer readable storage media including computer readable instructions which, when read and executed by a computing device, cause the computing device to:
- determine a workflow for capturing one or more eye images using an eye imaging device, the workflow determined based on a risk score for a given patient, wherein the risk score represents a likelihood of deterioration from a disease affecting macro vital signs;
- perform the workflow on the eye imaging device to capture the one or more eye images;
- conduct a microvascular assessment based on the captured eye images; and
- adjust the risk score based on the microvascular assessment to generate an enhanced risk score; and
- set a timer to trigger an alert to take additional eye images using the eye imaging device, wherein the timer is set based on the enhanced risk score.

15. The non-transitory computer readable storage media of claim 14, further comprising computer readable instructions which when read and executed by the computing device, cause the computing device to:
- adjust the workflow on the eye imaging device based on the microvascular assessment.

16. The non-transitory computer readable storage media of claim 14, further comprising computer readable instructions which when read and executed by the computing device, cause the computing device to:
- adjust the workflow on the eye imaging device based on a disease progress.

17. The non-transitory computer readable storage media of claim 16, wherein the workflow is adjusted to capture different quantities and types of eye images.

18. The system of claim 1, wherein the timer is set to have a shorter time interval causing the alert to be triggered more frequently when the enhanced risk score is high, and wherein the timer is set to have a longer time interval causing the alert to be triggered less frequently when the enhanced risk score is low.

19. The system of claim 1, wherein a time interval of the timer for triggering the alert decreases when the enhanced risk score increases from a previous risk score, and wherein the time interval of the timer for triggering the alert increases when the enhanced risk score decreases from the previous risk score.

* * * * *

UNITED STATES PATENT AND TRADEMARK OFFICE
CERTIFICATE OF CORRECTION

| | | |
|---|---|---|
| PATENT NO. | : 12,369,794 B2 | Page 1 of 1 |
| APPLICATION NO. | : 17/368041 | |
| DATED | : July 29, 2025 | |
| INVENTOR(S) | : Craig M. Meyerson et al. | |

It is certified that error appears in the above-identified patent and that said Letters Patent is hereby corrected as shown below:

In the Claims

In Claim 1, Line 28 of Column 16, after "eye images;" delete --and--.

In Claim 10, Line 11 of Column 17, after "eye images;" delete --and--.

In Claim 14, Line 2 of Column 18, after "eye images," delete --and--.

Signed and Sealed this
Thirtieth Day of September, 2025

John A. Squires
*Director of the United States Patent and Trademark Office*